(12) United States Patent
Roth

(10) Patent No.: US 6,916,337 B2
(45) Date of Patent: Jul. 12, 2005

(54) ROLLED STENT WITH WAVEFORM PERFORATION PATTERN

(75) Inventor: Noah M. Roth, San Clemente, CA (US)

(73) Assignee: Micro Therapeutics, Inc., Irvine, CA (US)

(*) Notice: Subject to any disclaimer, the term of this patent is extended or adjusted under 35 U.S.C. 154(b) by 125 days.

(21) Appl. No.: 10/174,095

(22) Filed: Jun. 18, 2002

(65) Prior Publication Data
US 2002/0151965 A1 Oct. 17, 2002

Related U.S. Application Data

(63) Continuation of application No. 09/487,412, filed on Jan. 18, 2000, now Pat. No. 6,406,490, which is a continuation of application No. 09/087,600, filed on May 29, 1998, now Pat. No. 6,015,433.

(51) Int. Cl.$^7$ ................................................. A61F 2/06
(52) U.S. Cl. ........................................................ 623/1.2
(58) Field of Search .............................. 623/1.22, 1.15, 623/1.19, 1.2

(56) References Cited

U.S. PATENT DOCUMENTS

| | | | |
|---|---|---|---|
| 5,306,286 A | 4/1994 | Stack et al. | 606/198 |
| 5,441,515 A | 8/1995 | Khosravi et al. | 606/194 |
| 5,443,500 A | 8/1995 | Sigwart | 623/1 |
| 5,449,382 A | 9/1995 | Dayton | 623/1 |
| 5,618,299 A | 4/1997 | Khosravi et al. | 606/198 |
| 5,632,840 A | 5/1997 | Campbell | 156/196 |
| 5,700,286 A | 12/1997 | Tartaglia et al. | 623/1 |
| 5,728,150 A | 3/1998 | McDonald et al. | 623/1 |
| 5,766,239 A | 6/1998 | Cox | 623/1 |
| 5,824,053 A | 10/1998 | Khosravi et al. | 623/1 |
| 5,824,054 A | 10/1998 | Khosravi et al. | 623/1 |
| 5,836,964 A | 11/1998 | Richter et al. | 606/194 |
| 5,938,682 A | 8/1999 | Hojeibane et al. | 606/198 |
| 6,015,433 A * | 1/2000 | Roth | 623/1.15 |
| 6,099,561 A | 8/2000 | Alt | 623/1.44 |
| 6,156,062 A | 12/2000 | McGuinness | 623/1.11 |
| 6,193,747 B1 | 2/2001 | Von Oepen | 623/1.15 |
| 6,406,490 B1 * | 6/2002 | Roth | 623/1.22 |

* cited by examiner

*Primary Examiner*—Alvin Stewart
(74) *Attorney, Agent, or Firm*—K. David Crockett, Esq.; Crockett & Crockett

(57) ABSTRACT

A stent fabricated from a rolled sheet. The sheet is perforated with wave form perforations to provide flexibility during insertion and in the body.

12 Claims, 3 Drawing Sheets

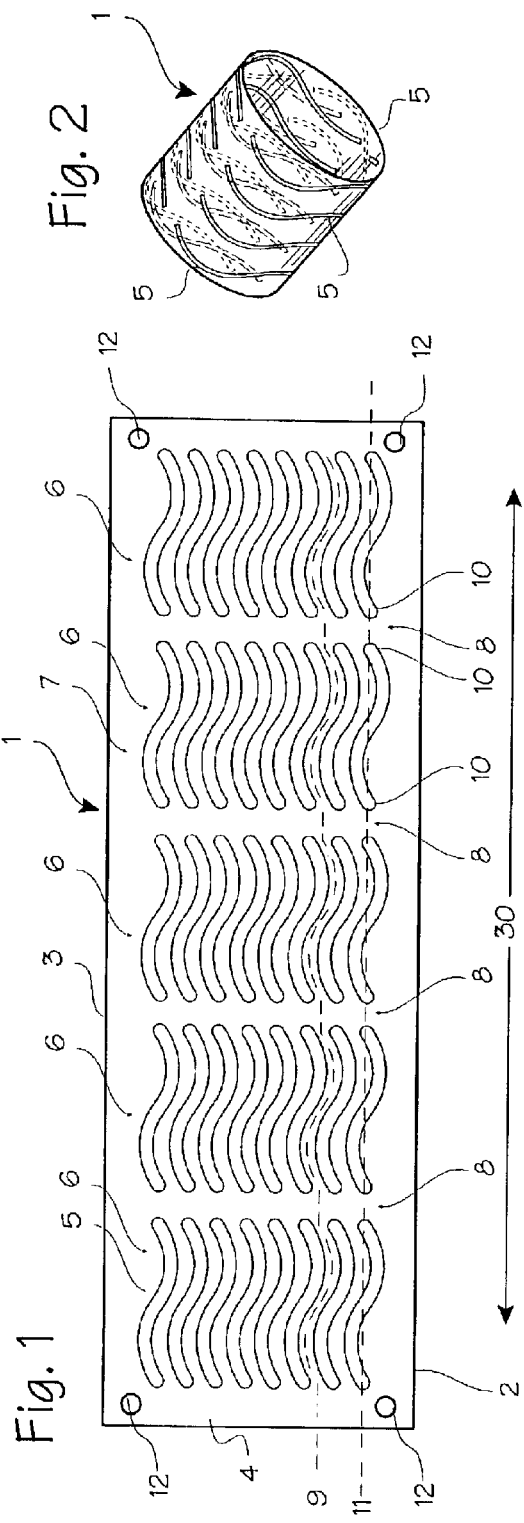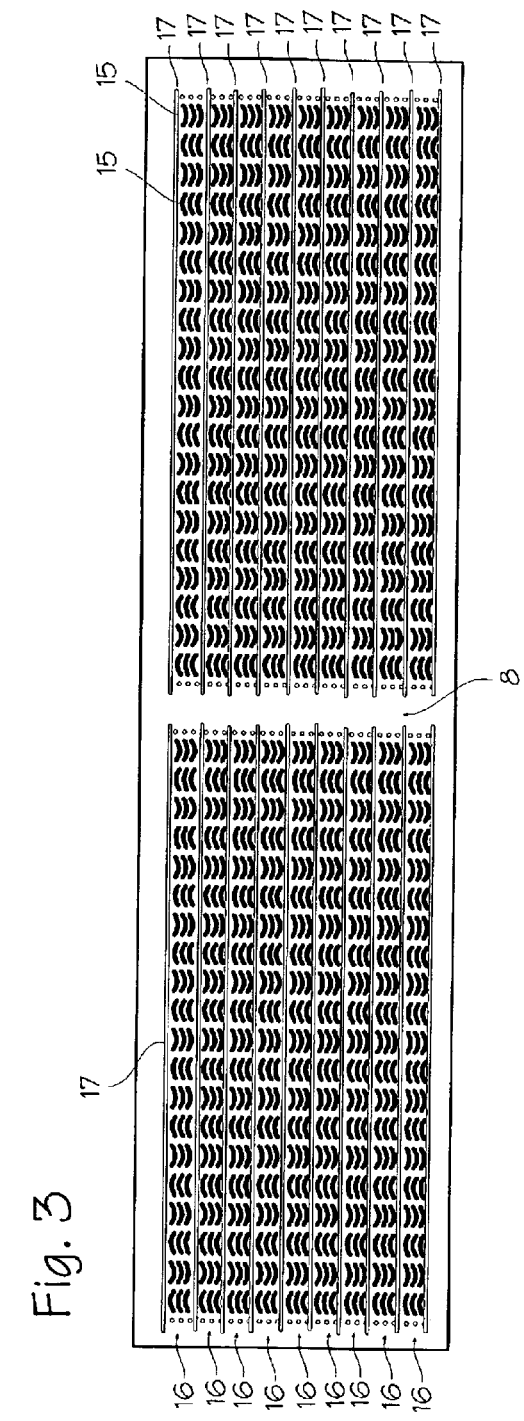

ROLLED STENT WITH WAVEFORM PERFORATION PATTERN

This application is a continuation of U.S. application Ser. No. 09/487,412 filed Jan. 18, 2000, now U.S. Pat. No. 6,406,490, which is a continuation of U.S. application Ser. No. 09/087,600 filed May 29, 1998, now U.S. Pat. No. 6,015,433.

FIELD OF THE INVENTIONS

This invention relates to treatments for vascular disease.

BACKGROUND OF THE INVENTIONS

In our prior patent applications, Intracranial Stent and Method of Use, U.S. patent application Ser. No. 08/707,996 (Sep. 18, 1996) and Ser. No. 08/761,110 (Dec. 9, 1996), we disclosed numerous embodiments of stents and stent delivery systems which enable surgeons to place stents deep within the brain. The inventions described in our prior applications were developed with the goal of providing new and better therapies for certain types of vascular disease for which the present day therapies are widely regarded as inadequate. Vascular disease includes aneurysms which can rupture and cause hemorrhage, atherosclerosis which can cause the occlusion of the blood vessels, vascular malformation and tumors. Occlusion of the coronary arteries, for example, is a common cause of heart attack. Vessel occlusion or rupture of an aneurysm within the brain are causes of stroke. Tumors fed by intra-cranial arteries can grow within the brain to the point where they cause a mass effect. The mass and size of the tumor can cause a stroke or the symptoms of stroke, requiring surgery for removal of the tumor or other remedial intervention.

Stents have not previously been used for aneurysms of the blood vessels in the brain. The vessels in the brain likely to develop stenosis, aneurysms, AVM's and side branches requiring occlusion have diameters of about 1 mm to 5 mm, and can be accessed only via highly tortuous routes through the vascular system. Instead, surgical clipping, resection, complete occlusion with acrylic-based adhesives (super glue) or small balloons (thereby intentionally occluding the downstream portion of the blood vessel and any portion of the brain supplied by that portion), stuffing with foreign objects, etc. have been used. In a method of current interest, small coils are stuffed into the aneurysm via a catheter. One such small coil is known as the Guglielmi Detachable Coil or GDC. After placement of a few coils, which partially obstruct blood flow in the aneurysm, the blood clots or fibrous matter forms within the sac. This technique has reportedly resulted in clots and coils falling out of the sac, and the technique is not used on wide-neck aneurysms. Aneurysm clipping, in which the skull is opened and the brain dissected to expose the outside of the aneurysm, followed by placement of clips at the base of the aneurysm, is also an option for treatment. However, these techniques do not always effect an immediate and complete seal of the aneurysm from the high pressure of the circulatory system, and rupture, leakage and deadly complications occur. Aneurysm rupture and bleeding during surgical clipping and shortly after the clip placement is a significant problem and add difficulty to the procedure. Examples of the problems inherent in the use of both GDC's and aneurysm clips are illustrated in Civit, et al., Aneurysm Clipping After Endovascular Treatment With Coils, 38 Neurosurgery 955 (May 1996) which reports that several patients in the study died after unsuccessful coil placement and before they could be re-treated with the open skull clip placement. Thus the article illustrates that GDC's do not always work, and when they fail they may leave the patient in a critical condition. As illustrated in the article, bleeding during surgical clipping and shortly after the clip placement is also a frequent problem.

From experiences like this, it is apparent that the ultimate goal of intracranial aneurysm treatment is the complete or nearly complete exclusion of the aneurysm cavity from the circulation, which prevents bleeding into the brain cavity and prevents formation of distal blood clots. This goal may be achieved immediately to ensure successful treatment by means of a substantially imperforate stent. It may also be achieved with a slightly perforated stent which alters flow in such a way that compete clotting, over time, is initiated within the aneurysm. It may also be achieved with a perforate stent through which embolic material such as coils are placed in the aneurysm. The treatments may be accomplished by placement of the stents described below which generally do not require the use of balloons for expansion of the stent, so that the blood vessel being treated is not occluded during placement of the stent.

Typically, the stents described below will be delivered percutaneously, introduced into the body through the femoral artery, steered upwardly through the aorta, vena cava, carotid or vertebral artery, and into the various blood vessels of the brain. Further insertion into the brain requires passage through the highly tortuous and small diameter intra-cranial blood vessels. The Circle of Willis, a network of blood vessels which is central to the intracranial vascular system, is characterized by numerous small arteries and bends. Passage of a stent from the internal carotid through the Circle of Willis and into the anterior cerebral artery (for example) requires a turn of about 60° through blood vessels of only 1–5 mm in diameter. Clinically, many significant aneurysms take place in the Circle of Willis and approaching blood vessels. The stent and delivery systems described herein are intended for use in such highly tortuous vessels, particularly in the Circle of Willis, the vertebral and carotid siphons and other major blood vessels of the brain. At times, pathologically tortuous vessels may be encountered in the deeper vessels of the brain, and these vessels may be characterized by small diameter, by branching at angles in excess of 90° and by inaccessibility with guide wires larger than the standard 0.018 guide-wires. These pathologically tortuous vessels may also be subject to aneurysms and AVM's which can be treated with the stents described below.

SUMMARY

Stents for intra-cranial use are described in detail below. The physical characteristics of prior art balloon expandable stents and self expanding stents make them clearly unsuitable for intra-cranial use, because of their delivery profile and tendency to temporarily occlude the vessel during deployment. They have not been proposed for intra-cranial use. Palmaz stents, Palmaz-Schatz™ stents, Wallstents, Cragg stents, Strecker stents and Gianturco stents and other stents are too rigid to allow placement in the cerebral blood vessels, some require a balloon for deployment, and all are too open to immediately occlude an aneurysm. Presented below are several embodiments of stents suitable for intra-cranial use.

The self expanding rolled sheet stent is suitable for use in the intra-cranial arteries. The rolled sheet is made of Elgiloy™, nitinol, stainless steel, plastic or other suitable material, and is imparted with resilience to urge outward expansion of the roll to bring the rolled stent into contact with the inner wall of a diseased artery. The rolled sheet is adapted for easy insertion and non-deforming radial flexibility to facilitate tracking along the tortuous insertion pathways into the brain. Much of the material of the stent is removed to create a highly perforated stent upon unrolling of the stent within the blood vessel. However, the material is removed in a pattern of perforations that leaves the stent with sufficient hoop strength to open and remain patent in the blood vessel. The unrolled stent may be two or more layers of Elgiloy™, thus providing radial strength for the stent and creating at least a slight compliance mismatch between the stent and the blood vessel, thereby creating a seal between the stent and the blood vessel wall. For placement, the stent is tightly rolled upon or captured within the distal tip of an insertion catheter. The stent can be placed in the intra-cranial blood vessels (arteries and veins) of a patient to accomplish immediate and complete isolation of an aneurysm and side branches from the circulatory system. The stent may be placed across a target site such as an aneurysm neck, origin of a fistula, or branch blood vessels feeding a tumor in order to redirect the flow of blood away from the target. It can be used as a stand alone device which is left in the intra-cranial artery permanently, or it may be used as a temporary device which allows for immediate stabilization of a patient undergoing rupture of a blood vessel an aneurysm or awaiting open skull surgery for clipping or resection of an aneurysm. The stent can be used for stabilization and isolation of a vascular defect during surgery of the vascular defect. Another advantage of this type of stent is that it can be wound down should repositioning be required prior to full release. It is possible to rewind and reposition or remove the device using grasping tools.

The stent described below is designed with perforation patterns which provide a rolled stent having desirable porosity and undercut pores which allow endothelial in-growth into the wall of the stent to assist in anchoring the stent into the blood vessel. The perforations on the unrolled stent are created and placed in sets of wave like patterns as illustrated in the Figures.

BRIEF DESCRIPTION OF THE DRAWINGS

FIG. 1 is an illustration of a stent with wave-form perforations.

FIG. 2 is an illustration of a stent with wave-form perforations shown in the rolled condition.

FIG. 3 is an illustration of a stent with wave-form perforations.

DETAILED DESCRIPTION OF THE INVENTIONS

Figure 4:
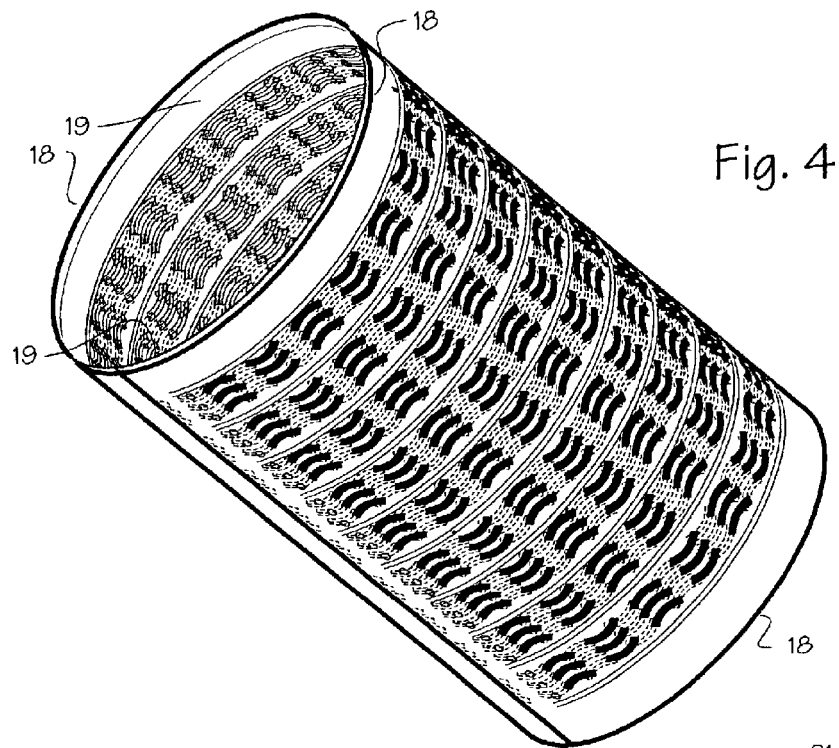
FIG. 4 is an illustration of the stent of FIG. 3 shown in the rolled condition.

FIG. 1 shows a basic form of the stent 1. The basic embodiment comprises a sheet 2 of Elgiloy™ about 0.0025 to 0.025 mm thick (0.1 mils to 1 mil, or 0.0001 to 0.0010 inches). Referring to FIG. 1, the wrap length represented by transverse edge 3 will be about 6–75 mm, allowing the stent to expand to diameters from about 1 mm to about 6 mm with approximately two to three layers after expansion. The bridge length represented by axial edge 4 (or the longitudinal edge) will vary according to the width of the aneurysm, occlusion or other defect which must be bridged by the stent, and may vary from 2 to 20 mm, for example. The stent is tempered or formed so that it resiliently unrolls and expands to a diameter of approximately 1 mm to 6 mm, and provides a slight compliance mismatch with the intra-cranial arteries which have internal diameters of about 1 mm to 6 mm.

The stent may be formed of Elgiloy™, nitinol, stainless steel, plastic or other suitable material. The stent, when formed of metal, is fabricated with the grain of the metal oriented in the circumferential direction indicated by arrow 30. The grain direction is imparted during the rolling process which is used to form the metal into such thin sheets. For rolling nitinol into sheets in the range of 0.0003 inches thickness (0.3 mil) and below, the stock material must be passed through a rolling mill numerous times. It is advantageous to roll the stock material in an oxygen free atmosphere, at elevated temperature of approximately 400° F., annealing between rolling steps at 500° F. for about an hour, and pickling the material in a bath of dilute hydrofloric acid after every second pass through the rolling mill. Finally, after the nitinol has nearly reached the desired thickness, it is pickled once more, then rolled again for smoothing. The process provides an extremely thin sheet with uniform composition of nitinol throughout, a smooth surface and uniform mechanical properties.

The stent perforations are preferably formed with a photochemical machining process which includes coating the sheet with a photoresist coating, processing the photoresist coating to remove the coating in areas corresponding to the desired perforations, thereby creating a partial coating which is a reverse image of the desired perforation pattern on the sheet, etching the metal in the uncoated areas with a chemical etchant to remove the metal in the areas corresponding to the desired perforation pattern, and then stripping the photoresist coating. This allows the creation of such thin sheets of metal without resort to mechanical cutting. Alignment of the circumferentially oriented perforations described below with the circumferentially oriented grain of the metal provides for easier deployment of the stent (the rolled sheet bends preferentially in the direction perpendicular to the grain).

When expanded, the stent intended for most intracranial applications will comprise a tube of one to three rolled layers. The stents described above can provide expansion ratios of five to one or greater. Expansion ratios of less than five to one may be achieved if desired. For particular intracranial applications, stents having more than three layers may be used. Stents of this configuration comprising less than a single layer when unrolled may also be useful. With the perforations provided as indicated below, the stent may be perforated over 80% of its surface area, while still maintaining sufficient hoop strength in the rolled configuration to maintain patency of blood vessels afflicted with various lesions, malformations and aneurysms.

Referring again to FIG. 1, the stent 1 is provided with a number of perforations 5. The perforations are wave-shaped or "s" shaped in general appearance. They may be formed more specifically as a series of partial sinusoidal curves. They may also be described as a longitudinal series of 6 of partial sinusoidal curves which are offset from adjacent longitudinal series 7 of partial sinusoidal curves. By longitudinal series, we mean a series of curves that extends along the longitude of the deployed stent. The curves themselves extend around the circumference of the stent, (they may be described as extending circumferentially, or as aligned generally with the wrap length), while the groups of curves 6a, 6b, . . . 6n extend along the bridge length 4 of the stent. The groups of curves creates longitudinal staves of un-perforated sheet material 8 which are relatively stiff compared to the perforated area. The curves are not significantly inclined away from or toward the wrap length or transverse edge 3, so that a multiple number of circumferentially extending and sinusoidally winding strips of sheet material are created, indicated by line 9. The strips are not perfectly sinusoidal, but may generally be described as sinusoidal, wavy, sinuous or wiggled in a manner where the long path of the strip is generally straight, but regularly deviates away from the long path. The continuous circumferential strips or bands of stent material provide increased hoop strength and dispersed stress concentrations for the sheet stent vis-à-vis arrangements in which the perforations are longitudinally aligned and interrupt circumferentially extending structure in the rolled sheet. In FIG. 1, end endpoints 10 of the perforations in respective sets are longitudinally aligned, meaning that they appear at the same point along the length 4 of the stent indicated by dotted line 11. The endpoints are radiused or curved, rather than sharply square, and this should serve to minimize stress within the stent during deployment and use. Note in FIG. 1 the retaining perforations 12 that are used to retain the stent on an insertion catheter.

FIG. 2 shows the stent 1 of FIG. 1 as it appears when rolled. The sinusoidal perforations 5 coincide to create some points of overlap which constitute gaps, contours and undercuts in the multi-layered thickness of the stent in the rolled condition. The result is a mesh or three-dimensional grate which provides surface area for ingrowth of blood vessel endothelial cells, which is beneficial to the acceptance and retention of the stent in the blood vessel.

FIG. 3 shows a more complicated version of the stent which incorporates the concept of curved or wave-form perforations. A multitude of perforations 15 are provided in sets 16 disposed between straight radial slits 17. The perforations are crescent or banana shaped. Specifically, the perforations shown are shaped as sinusoidal half-waves, and each sinusoidal half wave is radially adjacent to a corresponding and opposite sinusoidal half wave. The perforations are about 0.06–0.07 inches apart radially, and 0.1563 inches apart longitudinally, and they are about 0.03 inches wide and 0.0375 inches long. The exact sizes are not critical, but illustrated to communicate the approximate size of the desired perforations. The terminal point of each perforation is rounded, as shown in FIG. 3, to alleviate stress in the sheet. The sets 16 are circumferentially extending bands of perforations, aligned with the wrap length of the stent. A group of several perforation sets 16 are provided along the along the length of the stent. The perforations may be formed with electrolytic and chemical etching techniques, or by other suitable means. Several groups of sets are provided along the wrap length of the stent, leaving longitudinally oriented structural staves 8, which are areas of relative stiffness between the groups of perforation sets.

Figure 5:
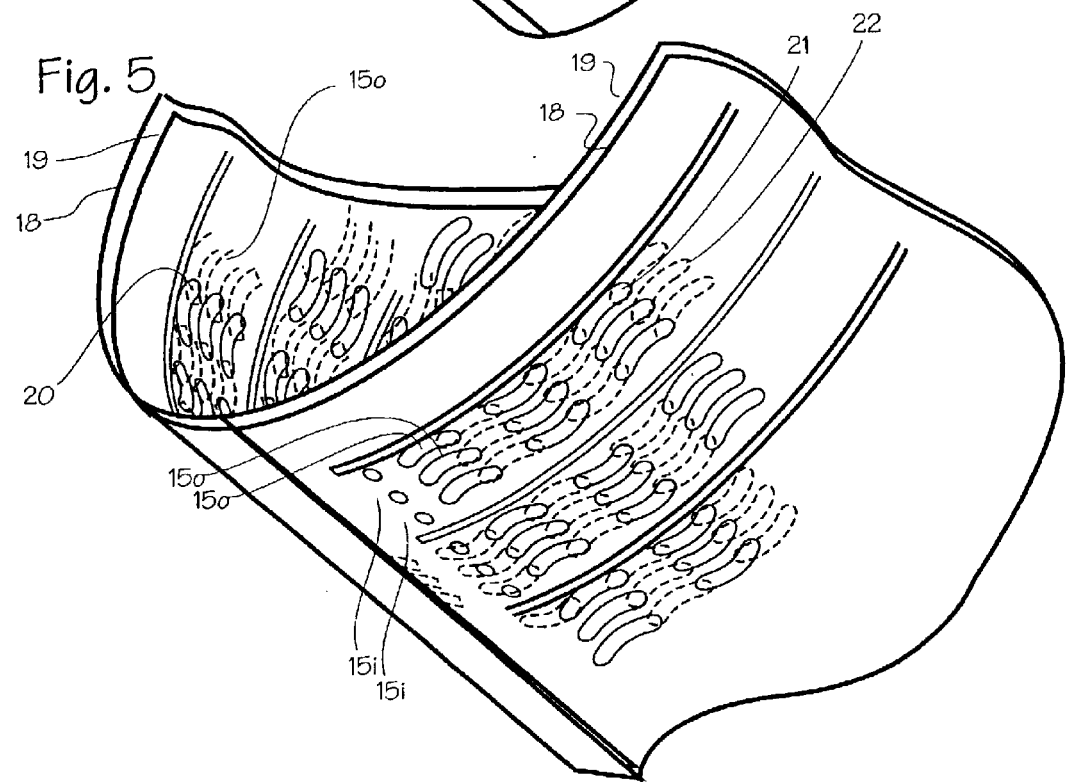
FIG. 5 is a close up view of the stent of FIG. 3 shown in the rolled condition.

FIG. 4 illustrates the stent of FIG. 3 when rolled. The many perforations in the outer layer 18 overlie the perforations of the inner layer 19. With two or more such layers, an array of gaps, partial gaps, and undercuts are formed in the overall structure of the rolled stent, leaving a matrix of stent material. These gaps and undercuts permit the growth of blood vessel endothelial cells within the matrix and on the inner lumenal surface of the stent. FIG. 5 is a close up view of the densely perforated stent when rolled as shown in FIG. 4. The overlap between perforations 15o on the outer layer 14 and perforations 15i on the inner layer 19 which lead to gaps 20 and undercut areas are more clearly visible in this figure. As can be seen in FIG. 5, the overlapping layers of wave-form perforated sheets create areas which are open, as in the area indicated by arrow 21. The overlapping layers of wave-form perforated sheets also create undercut areas (indicated by arrow 22) in which the intact portion of the sheet material of an outer layer overlaps a portion of a perforation on an immediately underlying layer, while an open portion of the sheet material in the same outer layer overlaps the same perforation in the underlying layer, thereby creating an undercut in the overall wall structure. In this manner, and irregular, porous and undercut structure is formed of a sheet of material such as metal which is not porous to biological tissue.

Figure 6:
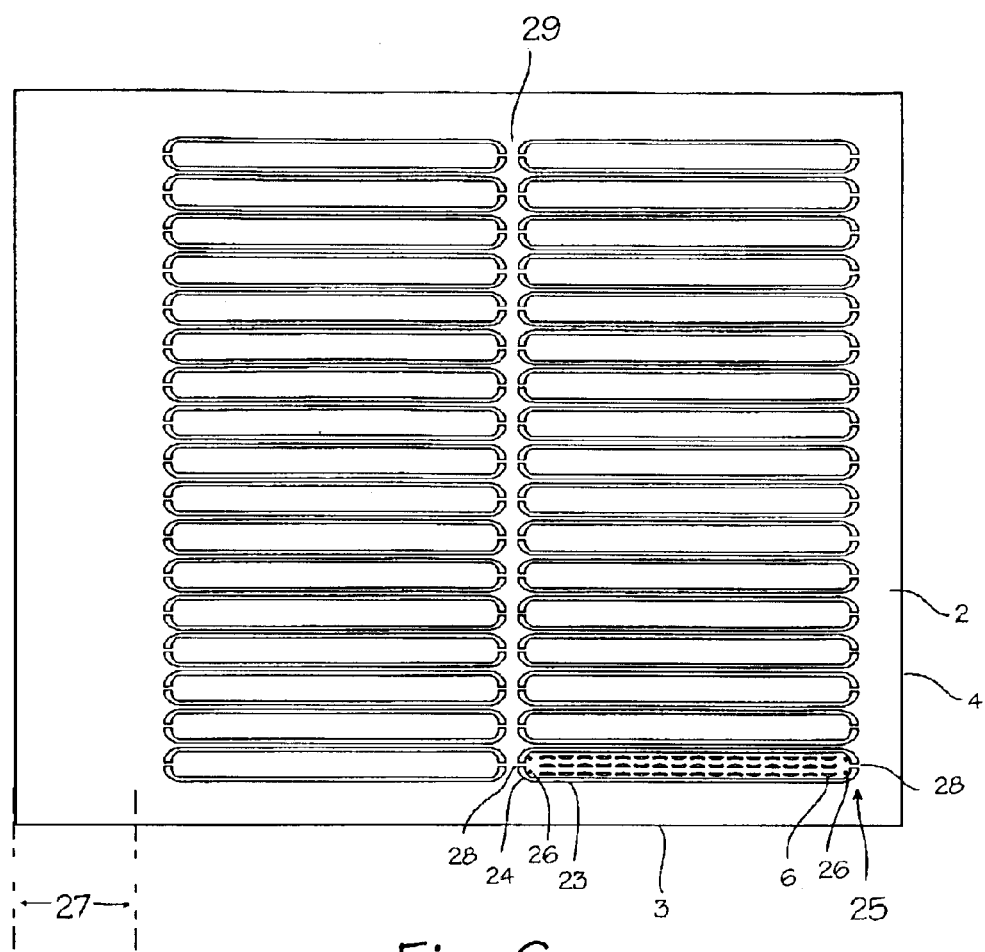
FIG. 6 is an illustration of a stent with wave-form perforations.
Figure 7:
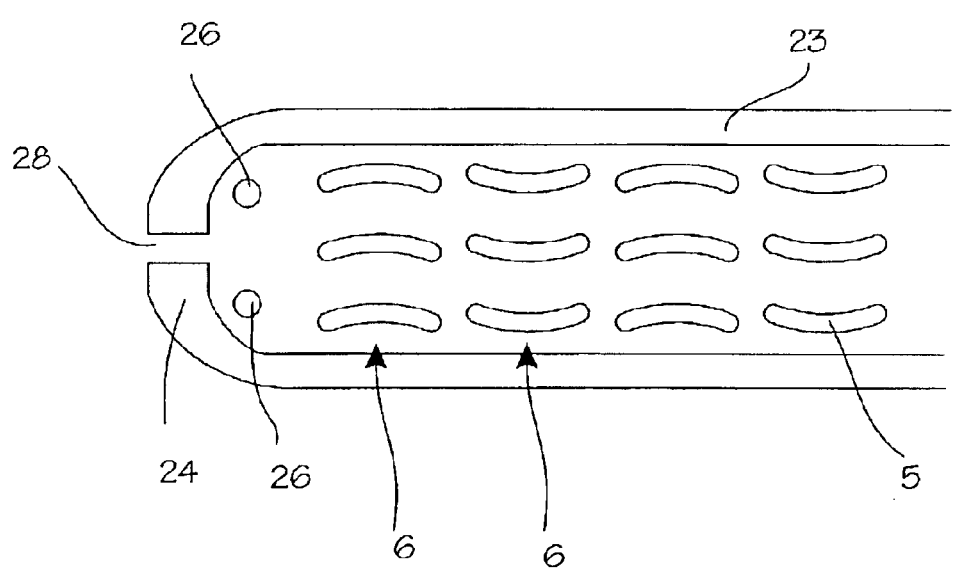
FIG. 7 is an illustration of a stent with wave-form perforations.

FIG. 6 illustrates an embodiment of the stent sheet 2 with features similar to the stent of FIG. 3 wherein the sets 16 of curved perforations 5 are bounded by the long radial or circumferential slits 23 which are generally straight in the circumferential direction, except for the curve 24 toward the longitudinal dimension of the stent which is incorporated at the terminus 25 of each radial slit 23. The rounded edges created in the radial end of the wave set areas help distribute the point force imparted on the vessel wall and reduces the risk of vascular injury that arises with the use of square edges. The pair of circular perforations 26 is provided for threading a retention/release wire through the stent sheet while rolled upon an insertion catheter. The sheet 2 includes a frame of sacrificial material 27 which is removed during manufacture to leave the stent in its implantable form. FIG. 7 shows a close-up of the perforation pattern near the terminus 25 of each set of perforations, including the terminal longitudinal curve 24 in each of the radial slits 23 which form a small connecting bridge 28 between the perforation set area and the stave area 29 (shown in FIG. 6). The terminal longitudinal curve is provided to alleviate stresses expected in a square perforation slit.

While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

I claim:

1. A stent comprising:
   a rolled sheet of material forming a tube having a plurality of layers, wherein said sheet is perforated with a plurality of perforations, said perforations are shaped as waveforms, and wherein perforations on each layer overlap perforations on each of the other layers to form gaps in the tube formed by the rolled sheet.

2. The stent of claim 1 wherein said rolled sheet of material is sized and proportioned to fit within a blood vessel of the brain of a patient.

3. The stent of claim 2 wherein the perforations comprise at least about 80% of the surface area of the rolled sheet.

4. The stent of claim 2 wherein the perforations are arranged in circumferentially extending bands around a circumference of the stent, and wherein a plurality of said circumferentially extending bands of perforations are disposed along the length of the stent.

5. The stent of claim 1 wherein the perforations comprise at least about 80% of the surface area of the rolled sheet.

6. The stent of claim 1 wherein the perforations are arranged in circumferentially extending bands around a circumference of the stent, and wherein a plurality of said circumferentially extending bands of perforations are disposed along the length of the stent.

7. A stent comprising:
a rolled sheet of material forming a tube having first and second layers, wherein said sheet is perforated with a plurality of perforations, said perforations are shaped as waveforms, wherein perforations on the first layer overlap perforations on the second layer to form gaps in the tube formed by the rolled sheet, and wherein said rolled sheet of material is sized and proportioned to fit within a blood vessel of the brain of a patient.

8. The intent of claim 7 wherein the perforations comprise at least about 80% of the surface area of the rolled sheet.

9. The stent of claim 7 wherein the perforations are arranged in circumferentially extending bands around a circumference of the stent, and wherein a plurality of said circumferentially extending bands of perforations are disposed along the length of the stent.

10. A stent comprising:
a sheet of material, said sheet being capable of rolling into a tubular structure having at least two layers, said sheet characterized by a transverse edge which, in the rolled tubular structure corresponds to the circumference of the stent, said sheet characterized by a longitudinal edge which, in the rolled tubular structure corresponds to the longitude of the stent;
said sheet being perforated by a plurality of perforations said perforations shaped as sinusoidal waves, said perforations being placed on the sheet so that a first group of said perforations are circumferentially aligned along a first longitudinal location on the intent, and a second group of said perforations are circumferentially aligned along a second longitudinal location on the stent, and subsequent groups of perforations are likewise circumferentially aligned along the length of the stent, thus forming a plurality of generally circumferentially extending sinuous hoops connected by longitudinally extending staves in the stent;
said sheet being sized and proportioned to fit within a blood vessel of the brain of a patient.

11. A method of treating a blood vessel in a patient, wherein said blood vessel has an aneurysm located on the wall of the blood vessel, said method comprising the steps of:
providing a stent comprising:
a sheet of material, said sheet being capable of rolling into a tubular structure having at least two layers, said sheet characterized by a transverse edge which, in the rolled tubular structure corresponds to the circumference of the stent, said sheet characterized by a longitudinal edge which, in the rolled tubular structure corresponds to the longitude of the stent;
said sheet being perforated by a plurality of perforations, said perforations shaped as sinusoidal waves, said perforations being placed on the sheet so that a first group of said perforations are circumferentially aligned along a first longitudinal location on the stent, and a second group of said perforations are circumferentially aligned along a second longitudinal location on the stent, and subsequent groups of perforations are likewise circumferentially aligned along length of the stent, thus forming a plurality of generally circumferentially extending sinuous hoops connected by longitudinally extending staves in the stent;
percutaneously inserting the stent into the blood vessel and positioning the stent so that the stent bridges the aneurysm; and
releasing the stent within the blood vessel.

12. The method of claim 11 wherein the blood vessel is disposed within the brain of the patient.

* * * * *